United States Patent
Oomori et al.

(10) Patent No.: US 7,758,573 B2
(45) Date of Patent: Jul. 20, 2010

(54) BLOOD VESSEL TREATMENT METHOD USING MULTI-DEGREE-OF-FREEDOM FORCEPS

(75) Inventors: Shigeru Oomori, Ashigarakami-gun (JP); Makoto Jinno, Tokyo (JP)

(73) Assignees: Terumo Kabushiki Kaisha, Tokyo (JP); Kabushiki Kaisha Toshiba, Tokyo (JP)

( * ) Notice: Subject to any disclaimer, the term of this patent is extended or adjusted under 35 U.S.C. 154(b) by 584 days.

(21) Appl. No.: 11/258,844

(22) Filed: Oct. 27, 2005

(65) Prior Publication Data

US 2007/0095355 A1 May 3, 2007

(51) Int. Cl.
*A61B 18/18* (2006.01)
*A61B 18/14* (2006.01)

(52) U.S. Cl. .............. 606/32; 606/51; 606/52

(58) Field of Classification Search .......... 606/32, 606/190, 51, 52; 600/103, 114; 128/898
See application file for complete search history.

(56) References Cited

U.S. PATENT DOCUMENTS

| | | | | |
|---|---|---|---|---|
| 5,022,414 A | * | 6/1991 | Muller | 128/898 |
| 5,147,356 A | * | 9/1992 | Bhatta | 606/37 |
| 6,001,108 A | | 12/1999 | Wang et al. | |
| 6,858,003 B2 | * | 2/2005 | Evans et al. | 600/103 |
| 6,889,116 B2 | | 5/2005 | Jinno | |
| 2003/0045778 A1 | * | 3/2003 | Ohline et al. | 600/114 |
| 2004/0267406 A1 | | 12/2004 | Jinno | |
| 2005/0096694 A1 | * | 5/2005 | Lee | 606/205 |
| 2005/0222587 A1 | | 10/2005 | Jinno et al. | |
| 2006/0074444 A1 | * | 4/2006 | Lin et al. | 606/190 |

FOREIGN PATENT DOCUMENTS

JP 2000-350735 12/2000
JP 2001-276091 10/2001

* cited by examiner

*Primary Examiner*—Lee S Cohen
(74) *Attorney, Agent, or Firm*—Oblon, Spivak, McClelland, Maier & Neustadt, L.L.P.

(57) ABSTRACT

A blood treatment method using high-degree-of-freedom forceps. The forceps main body includes a joint portion and a tip working portion provided on a distal end portion, a handle provided on a proximal end, which is held and manipulated, and an input portion provided on the handle. The controller drives the joint portion and the tip working portion with at least 2 degrees of freedom and in response to an input to the input portion. In the blood vessel treatment method, a membranous tissue covering a blood vessel is incised, the blood vessel is detached from the tissue, a branch is cut off from the blood vessel, or a peripheral side of the blood vessel is cut off, by respective inputs to the input portion, in the state where a distal side of the forceps main body is inserted into the body cavity.

15 Claims, 8 Drawing Sheets

BLOOD VESSEL TREATMENT METHOD USING MULTI-DEGREE-OF-FREEDOM FORCEPS

BACKGROUND OF THE INVENTION

1. Field of the Invention

The present invention relates to a blood vessel treatment method which treats a blood vessel in the body cavity, under observation with an endoscope.

2. Description of the Related Art

In endoscopic surgical operations, a plurality of holes are formed in the body wall, and tubular instruments such as trocars are inserted therethrough. Then, an endoscope and forceps are inserted into the body cavity with the tubular instruments used as ports, to perform observation and treatment of tissue in the body cavity.

As such an endoscopic surgical operation, used is an operation method in which the surgeon directly holds and manipulates conventional forceps. In such an operation method, the surgeon holds and manipulates a handle at a proximal end portion of a shaft of the forceps, and inserts the shaft into the body cavity through the port. Further, the shaft is moved back and forth in its longitudinal direction and rotated with the port used as a pivot, and thereby a tip working portion at a distal end portion of the shaft, such as a blade of an electric cautery, a gripper and scissors is driven, and treatment is performed by the tip working portion.

Further, U.S. Pat. No. 6,001,108 discloses an operation method in which forceps are held and manipulated in a remote-control-type master-slave mode. In such an operation method, the surgeon manipulates an operating handle while observing the affected area on a TV monitor, in a workstation away from the operation bed. Following the manipulation of the operating handle, a multi-joint robot arm disposed in the vicinity of the operation bed is activated, and forceps held by the multi-joint robot arm is inserted into the body cavity through the port. Further, following manipulation of the operating handle, the tip working portion is driven, and treatment is performed by the tip working portion.

Jpn. Pat. Appln. KOKAI Pub. No. 2001-276091 discloses multi-degree-of-freedom forceps used for endoscopic surgical operations. A joint portion is arranged between a distal end portion of a shaft and a tip working portion in the multi-degree-of-freedom forceps. The joint portion is activated following manipulation to a joystick and the like provided on the handle, and drives the tip working portion with multi degree of freedom.

Such multi-degree-of-freedom forceps can be used for various cases, since the tip working portion thereof has a higher degree of freedom than those of common forceps. Further, in comparison with the remote-control-type master-slave mode surgical operation, the multi-degree-of-freedom forceps surgical operation simplifies preparation of the operation since it is unnecessary to position and fix a multi-joint robot arm before the operation and makes no limitation of applicable cases due to necessity of determining the position of the multi-joint robot arm before the operation.

Although multi-degree-of-freedom forceps have such advantages, Jpn. Pat. Appln. KOKAI Pub. No. 2001-276091 neither describes nor suggests for what cases multi-degree-of-freedom forceps are effectively used.

BRIEF SUMMARY OF THE INVENTION

According to an aspect of the present invention, there is provided a blood vessel treatment method using multi-degree-of-freedom forceps. The multi-degree-of-freedom forceps comprises a forceps main body and a controller. The forceps main body includes an elongated inserting portion, a joint portion provided on a distal end portion of the inserting portion, a tip working portion which is connected to the joint portion and driven with at least 2 degrees of freedom by activation of the joint portion, a handle provided on a proximal end portion of the inserting portion, which includes an actuator activating the joint portion and the tip working portion and is held and manipulated, and an input portion provided on the handle. The controller transmits an electric signal to the actuator and drives the joint portion and the tip working portion in response to an input to the input portion. In the blood vessel treatment method, a membranous tissue covering a blood vessel is incised, the blood vessel is detached from the tissue, a branch is cut off from the blood vessel, or a peripheral side of the blood vessel is cut off, by respective inputs to the input portion, in the state where a distal side of the forceps main body is inserted into the body cavity.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
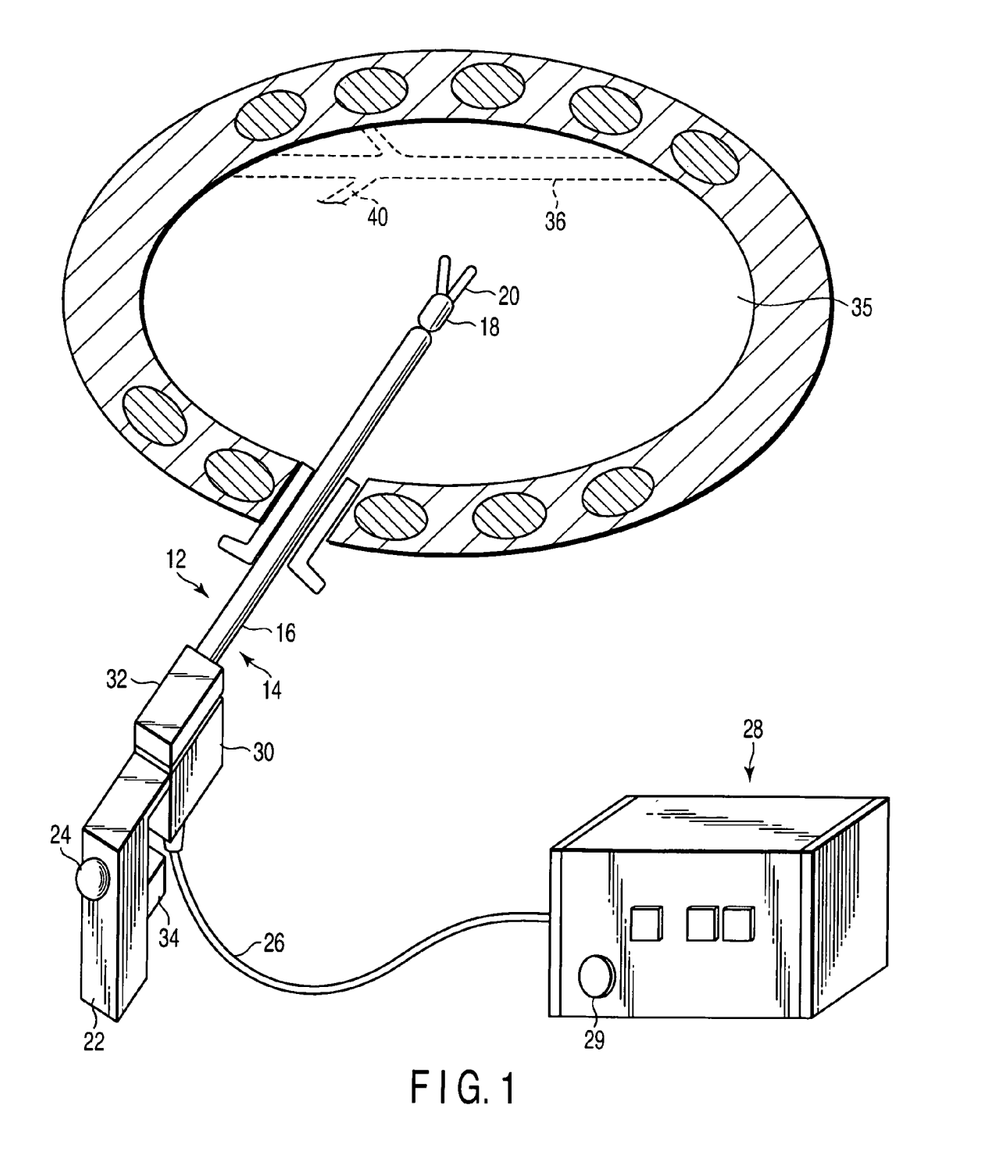
FIG. 1 is a schematic diagram illustrating a step of inserting a distal side of forceps main body into the body cavity, in a blood vessel treatment method according to an embodiment of the present invention.

With reference to FIG. 1, explained is a multi-degree-of-freedom forceps 12 used for a blood vessel treatment method according to an embodiment of the present invention. The multi-degree-of-freedom forceps 12 has a forceps main body 14. The forceps main body 14 has a shaft 16 serving as an elongated inserting portion to be inserted into the body cavity.

A joint portion 18 is arranged on a distal end portion of the shaft 16, and a tip working portion 20 is connected to the joint portion 18. By activating the joint portion 18, the tip working portion 20 is driven with 2 degrees of freedom. In the embodiment, the tip working portion 20 is driven in two directions which are perpendicular to the central axis of the shaft 16 and also perpendicular to each other. In the following explanation, the two directions are referred to as "vertical direction" and "horizontal direction" hereinafter. As the tip working portion 20, used are a blade of an electric cautery, a gripper, scissors, and an anastomotic needle in the embodiment, according to the steps of the blood vessel treatment method.

A handle 22 is provided in a proximal end portion of the shaft 16. The handle 22 extends downward almost perpendicular to the central axis of the shaft 16. The surgeon can move the whole forceps main body 14 by holding the handle 22 by one hand.

A track ball 24 is provided with a proximal surface of the handle 22. The track ball 24 serves as an input portion to activate the joint portion 18 to drive the tip working portion 20. The track ball 24 is disposed such that it can be rotate-manipulated by the thumb of the hand holding the handle 22. Input to the track ball 24 is outputted to a controller 28 connected to an electric wiring cable 26 extended from the forceps main body 14. The controller 28 drives a plurality of motors to rotate in a motor housing 30 provided in the proximal end portion of the forceps main body 14. The motors rotate respective corresponding pulleys in a pulley housing 32 provided adjacent to the motor housing 30. The driven pulleys activate the joint portion 18 through the wire inserted through the shaft 16 to drive the tip working portion 20. A computer is included in the controller 28, and the computer calculates the rotation amount of the motors which achieves drive of the tip working portion 20 in the vertical and horizontal directions, in accordance with the rotation-manipulation of the track ball 24 in the vertical and horizontal directions. Further, it is possible to rotate the track ball 24 in a slanting direction by combining the vertical rotation and the horizontal rotation. In response to the slanting rotation of the track ball 24, the tip working portion 20 is driven in the slanting direction.

Further, a distal surface of the handle 22 is provided with a knob 34 which activates the tip working portion 20. The knob 34 is disposed such that it can be pushed in by a finger other than the thumb of the surgeon's hand holding the handle 22. Just like the input to the track ball 24, input to the knob 34 is outputted to the controller 28, then, the controller 28 drives the motors to rotate, and the tip working portion 20 is activated through the pulleys and the wire. For example, if the tip working portion 20 is a gripper or scissors, the gripper or the scissors are closed by pushing the knob 34.

If the tip working portion 20 is a blade of an electric cautery, the forceps main body 14 is connected to the electric cautery main body. Then, the electric cautery main body charges the blade with electricity by pressing down a foot switch connected to the electric cautery main body.

In the embodiment, the track ball 24 is used as the input portion 24 to drive the tip working portion 20 with 2 degrees of freedom. The input portion may adopt any form as long as it allows input operation of at least 2 degrees of freedom by a fingertip of the hand holding the handle 22. For example, the input portion may be a joystick, a quartered switch, and a switch in notch form or flat pad having a force sensing function. As another example, the input portion may have a pressure sensor and drive the tip working portion 20 with the magnitude in accordance with the applied pressure.

Next, the blood vessel treatment method of the present invention is explained. In the embodiment, a heart coronary artery bypass operation is explained as an example. However, the present invention is applicable to various blood vessels, and applicable to operations other than bypass operations. In the heart coronary artery bypass operation of the embodiment, in the state where the distal side of the forceps main body is inserted into the body cavity, an internal thoracic artery is stripped and a stump portion of the stripped internal thoracic artery is anastomosed to a heart coronary artery. Although an anastomosing step is performed since the bypass operation is explained in the embodiment, there are cases where an anastomosing step is not performed according to the type of the operation.

As shown in FIG. 1, in an operation, an endoscope is inserted into the body cavity with a tracor used as a port, to keep a region to be treated of an internal thoracic artery in view. Further, the electric wiring cable 26 of the forceps main body 14 is connected to the controller 28, and controller 28 is started in advance by turning on a power switch 29 of the controller 28.

Explained is a step of inserting the distal side of the forceps main body 14 into the thoracic cavity in the heart coronary artery bypass operation. The handle 22 of the forceps main body 14 is held and manipulated by one hand, and the tip working portion 20, the joint portion 18, and the shaft 16 of the forceps main body 14 are successively inserted into a thoracic cavity 35 with the tracor used as the port. Then, the shaft 16 is moved forward and backward in a direction of the central axis thereof and rotated with the port used as a pivot so that the tip working portion 20 at the distal end portion of the shaft 16 is positioned in the vicinity of the region to be treated and within the field of view of the endoscope (not shown).

Figure 2:
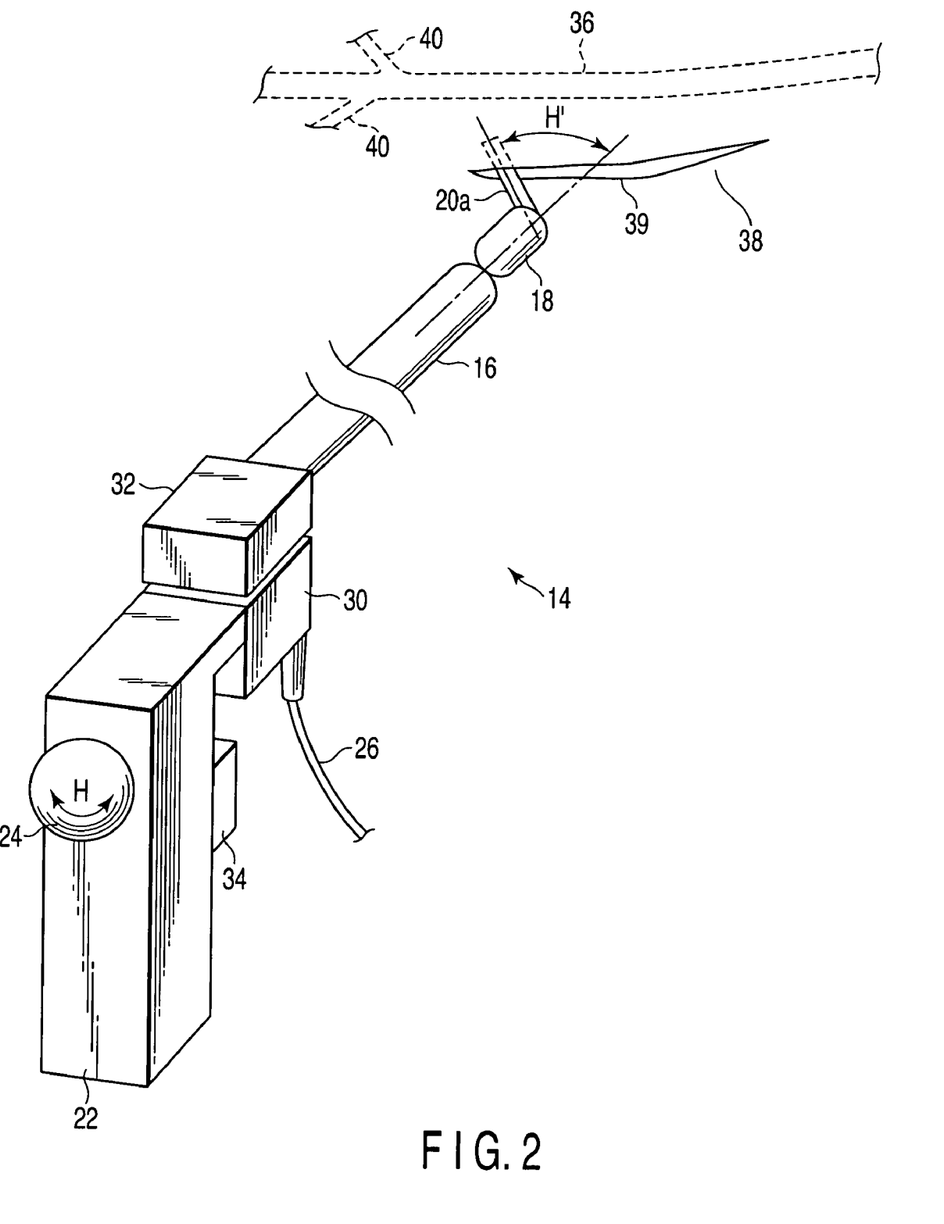
FIG. 2 is a perspective view illustrating a step of incising a membranous tissue covering an internal thoracic artery in the blood vessel treatment method according to the embodiment of the present invention.

Next, explained is an internal thoracic artery stripping in the heart coronary artery bypass operation, with reference to FIGS. 2 to 6. FIG. 2 illustrates a step of incising a membranous tissue 38 covering a internal thoracic artery 36 in internal thoracic artery stripping. In this step, a blade 20a of an electric cautery is used as the tip working portion of the forceps main body 14.

The distal side of the forceps main body 14 is inserted into the thoracic cavity by manipulating the handle 22, and the blade 20a is positioned in the vicinity of the membranous tissue 38 covering the to-be-treated region of the internal thoracic artery 36. The positioning is to be performed such that the horizontal direction of the forceps main body 14 almost agrees with the running direction of the internal thoracic artery 36. Thereafter, the electric cautery main body is started by pressing down the foot switch, and the electric cautery main body charges the blade 20a with electricity. Then, the track ball 24 is rotated in the horizontal direction (refer to arrow H in FIG. 2) by the surgeon's thumb while the handle 22 is held by one hand. Thereby, the joint portion 18 is activated, and the blade 20a is driven in the horizontal direction (refer to arrow H' in FIG. 2) to incise the membranous tissue 38 in the running direction of the internal thoracic artery 36. The internal thoracic artery 36 is exposed through an incision wound 39 generated.

Figure 3:
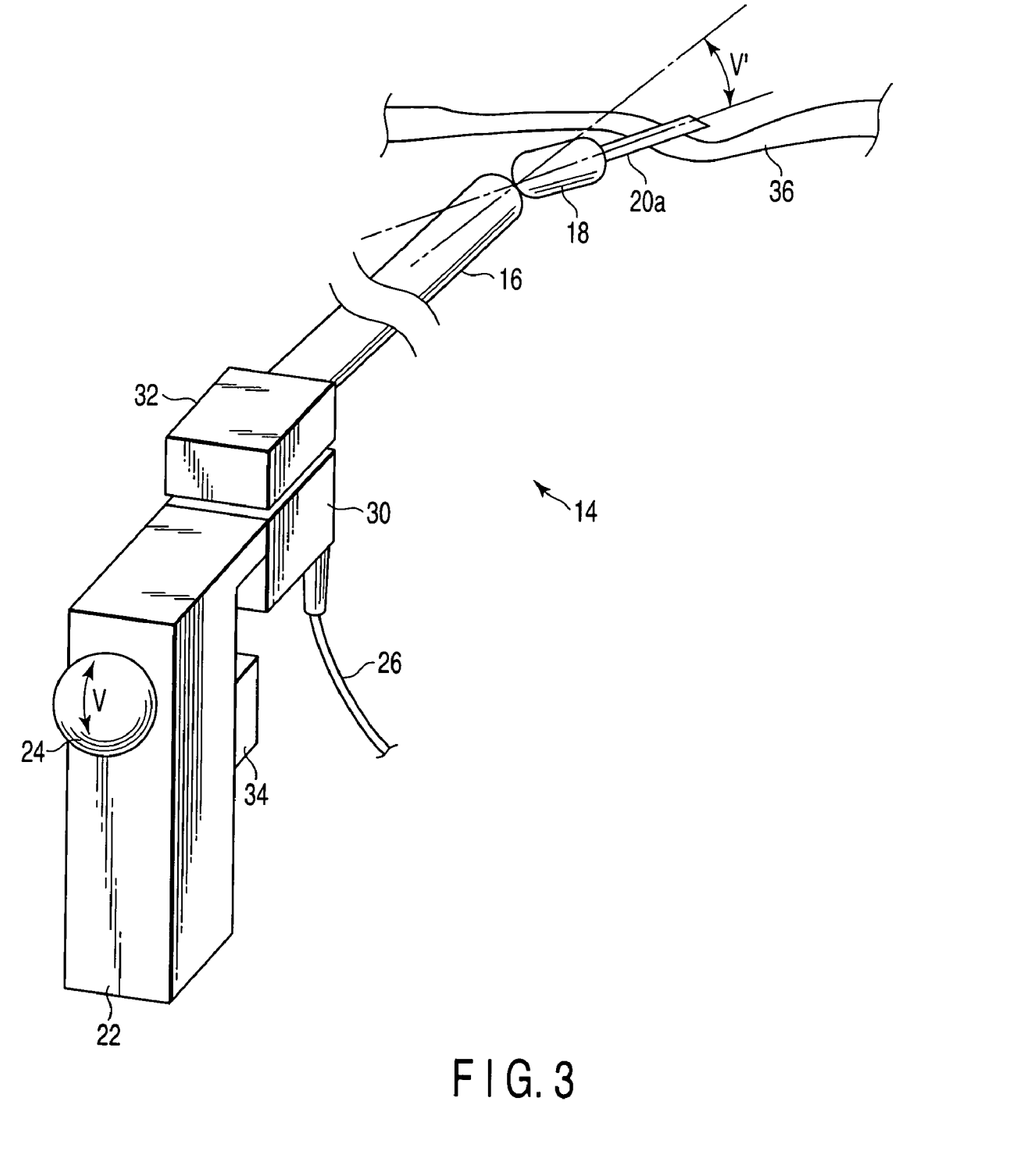
FIG. 3 is a perspective view illustrating a step of detaching the internal thoracic artery in the blood vessel treatment method according to the embodiment of the present invention.

FIG. 3 illustrates a step of detaching the internal thoracic artery 36 from a thorax in the internal thoracic artery stripping. Following the incision step, the track ball 24 is rotated in the vertical direction (refer to arrow V in FIG. 2) by the surgeon's thumb while the handle 22 is held by one hand, to activate the joint portion 18 to drive the blade 20a in the vertical direction (refer to arrow V' in FIG. 2). Then, a step of pushing down the exposed internal thoracic artery 36 is repeated by using the blade 20 like a spatula, and thereby the internal thoracic artery 36 is detached from the thorax.

Figure 4:
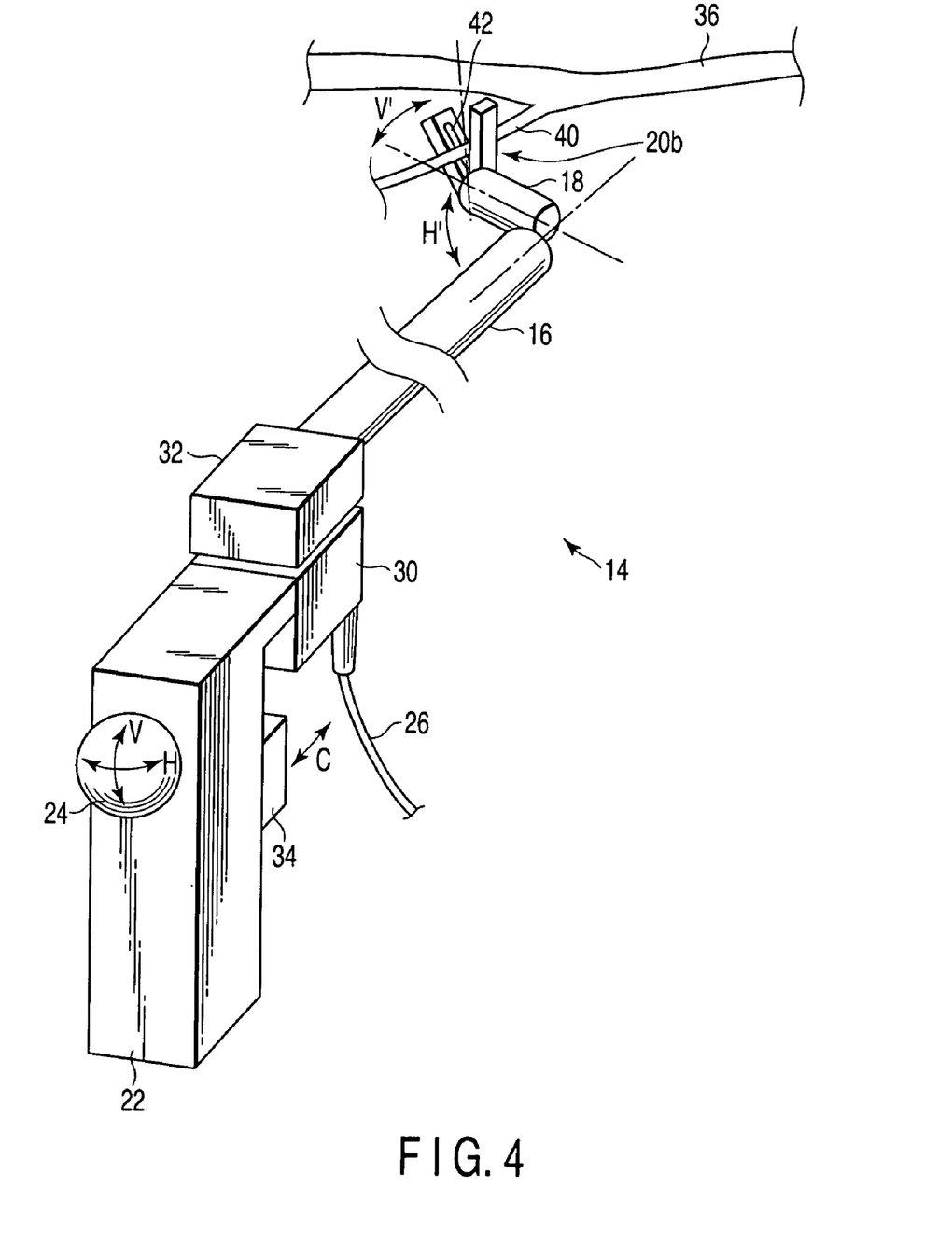
FIG. 4 is a perspective view illustrating a step of providing hemostasis to a branch in the blood vessel treatment method according to the embodiment of the present invention.
Figure 5:
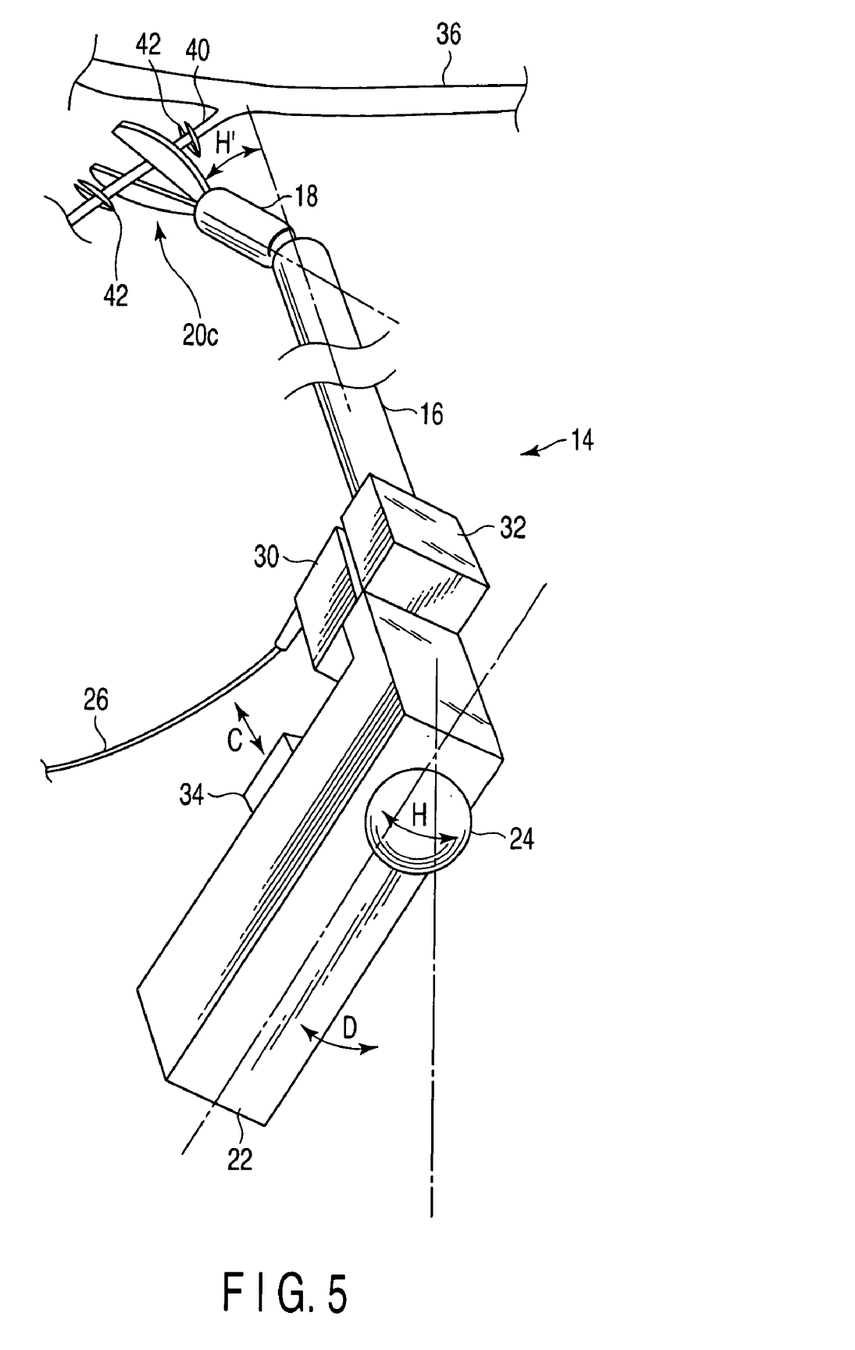
FIG. 5 is a perspective view illustrating a step of cutting off the branch in the blood vessel treatment method according to the embodiment of the present invention.

FIGS. 4 and 5 illustrate a step of cutting off a branch 40 from the internal thoracic artery 36 in the internal thoracic artery stripping. FIG. 4 illustrates a step of providing hemostasis of the branch 40 on both sides of a to-be-cut region before cutting. In this step, a gripper 20b is used as the tip working portion to caulk a hemostatis clip 42. The clip 42 in an opened state is set inside the gripper 20b, and caulked by closing the gripper 20b by pushing in the knob 34 (refer to arrow C in FIG. 4) of the forceps main body 14.

The distal side of the forceps main body 14 is inserted into the thoracic cavity, and the gripper 20b is positioned in the vicinity of one side of the to-be-cut region by manipulation of the handle 22. Then, the track ball 24 is rotated in the horizontal direction (refer to arrow H in FIG. 4) and the vertical direction (refer to arrow V in FIG. 4), and thereby the gripper 20b is driven in the horizontal direction (refer to arrow H' in FIG. 4) and the vertical direction (refer to arrow V' in FIG. 4) so that gripper 20b is positioned to be almost perpendicular to the running direction of the branch 40. Then, the handle 22 is slightly manipulated to position the gripper 20b so that the branch 40 is sandwiched by the gripper 20b and the clip 42. In this state, the knob 34 is pushed in by the surgeon's finger other than the thumb while the handle 22 is held by the hand, the clip 42 is caulked by closing the gripper 20b, and thereby the clip 42 is put over the branch 42 to shut off the bloodstream of the branch 40. In the same manner, a clip 42 is put over the branch 40 on the other side of the to-be-cut region. Thereby, the branch 40 is provided with hemostasis on the both sides of the to-be-cut region of the branch 40.

FIG. 5 illustrates a step of cutting off the branch 40 from the internal thoracic artery 36. In this step, scissors 20c are used as the tip working portion. The scissors 20c can be closed by pushing in the knob 34 of the forceps main body 14.

The distal side of the forceps main body 14 is inserted into the thoracic cavity by manipulating the handle 22, and the scissors 20c is positioned in the vicinity of the to-be-cut region. Then, the track ball 24 is rotated in the horizontal direction (refer to arrow H in FIG. 5), and thereby the scissors 20c are driven in the horizontal direction (refer to arrow H' in FIG. 5), and simultaneously, the handle 22 is rotated (refer to arrow D in FIG. 5) to rotate the shaft 16 around the central axis thereof, and thereby the scissors 20c are rotated around the central axis of the shaft 16, so that the scissors 20c is positioned such that the scissors 20c is almost perpendicular to the running direction of the branch 40 and the to-be-cut region of branch 40 is sandwiched by the scissors 20c. In this state, the knob 34 is pushed in (refer to arrow C in FIG. 5) to close the scissors 20c, and thereby the branch 40 is cut off from the internal thoracic artery 36.

If the branch 40 is cut off from the internal thoracic artery 36 by coagulation incision, hemostasis by the clips 42 is unnecessary. If the branch 40 is cut off by using an ultrasonic knife, hemostasis by the clips 42 is also unnecessary.

Figure 6:
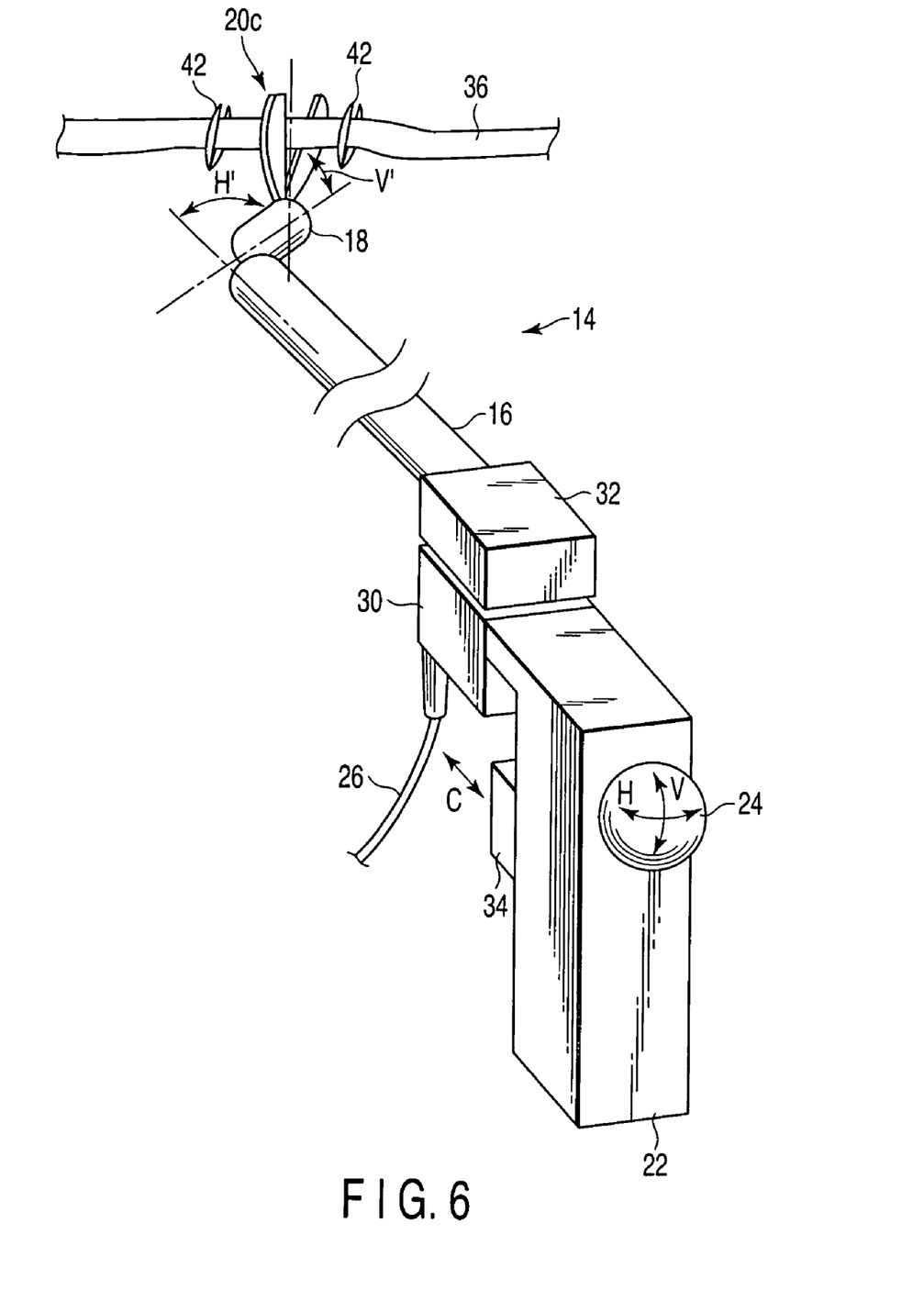
FIG. 6 is a perspective view illustrating a step of cutting off a peripheral side of the internal thoracic artery in the blood vessel treatment method according to the embodiment of the present invention.

FIG. 6 illustrates a step of cutting off the peripheral side of the internal thoracic artery 36. This step is basically the same as the step of cutting off a branch. In this step, the both sides of the to-be-cut region of the internal thoracic artery 36 is provided with hemostasis by the clips 42, the peripheral side of the internal thoracic artery 36 is cut off by the scissors 20c. In this step, the handle 22 is manipulated to position the scissors 20c in the vicinity of the to-be-treated region. Then, the track ball 24 is rotated in the horizontal direction (refer to arrow H in FIG. 6) and the vertical direction (refer to arrow V in FIG. 6) to drive the scissors 20c in the horizontal direction (refer to arrow H' in FIG. 6) and the vertical direction (refer to arrow V' in FIG. 6), so that the scissors 20c are positioned such that the scissors 20c is almost perpendicular to the running direction of internal thoracic artery 36 and the internal thoracic artery 36 is sandwiched by the scissors 20c.

Figure 7:
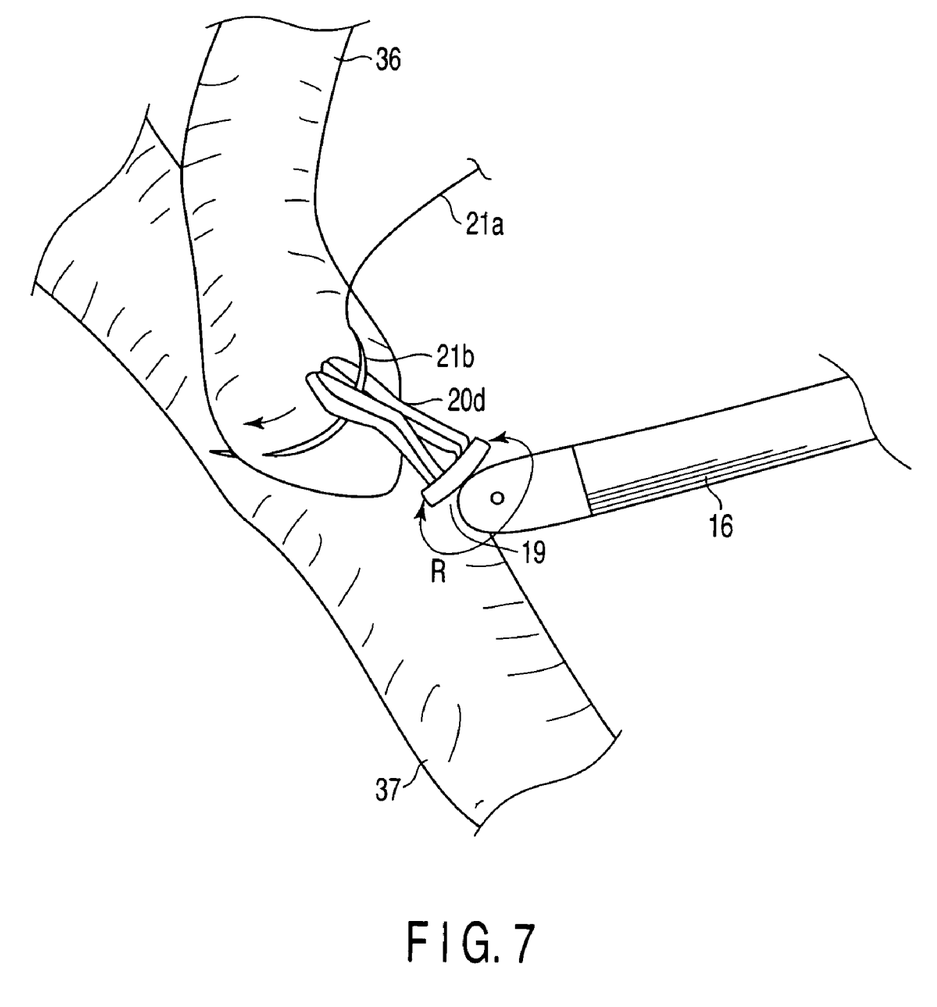
FIG. 7 is a perspective view illustrating a step of anastomosing a stump portion of the internal thoracic artery to a heart coronary artery, in the blood vessel treatment method according to the embodiment of the present invention.

FIG. 7 is a step of anastomosing a stump portion of the internal thoracic artery 36 to a heart coronary artery in the heart coronary artery bypass operation.

In this step, a special gripper 20d for holding a needle is used as the tip working portion. The gripper 20d holds an anastomotic needle 21b integrated with a suture 21a for suturing the living body. And the gripper 20d is driven in the horizontal direction by rotating the track ball 24 in the horizontal direction and rotated around the central axis of the joint potion 19 (refer to arrow R in FIG. 7) by rotating the track ball 24 in the vertical direction, in the distal end potion of the shaft 16.

As shown in FIGS. 1 and 7, the handle 22 is manipulated to position the gripper 20d, which is provided on the distal end potion of the forceps main body 14 inserted in the thoracic cavity, in the vicinity of a to-be-anastomosed region. Then, the track ball 24 is rotated in the horizontal direction and the vertical direction to drive the gripper 20d in the horizontal direction and rotate the gripper 20d, and thereby the direction of the gripper 20d is adjusted so that anastomotic needle 21b is turn in an desired suture-direction. Following that, the track ball 24 is rotated in the vertical direction to rotate the gripper 20d so that the anastomotic needle 21b is punctured through a stump portion of the internal thoracic artery 36 whose distal side has been cut off and a heart coronary artery 37, and thereby anastomosis is performed by means of the suture 21a.

Figure 8:
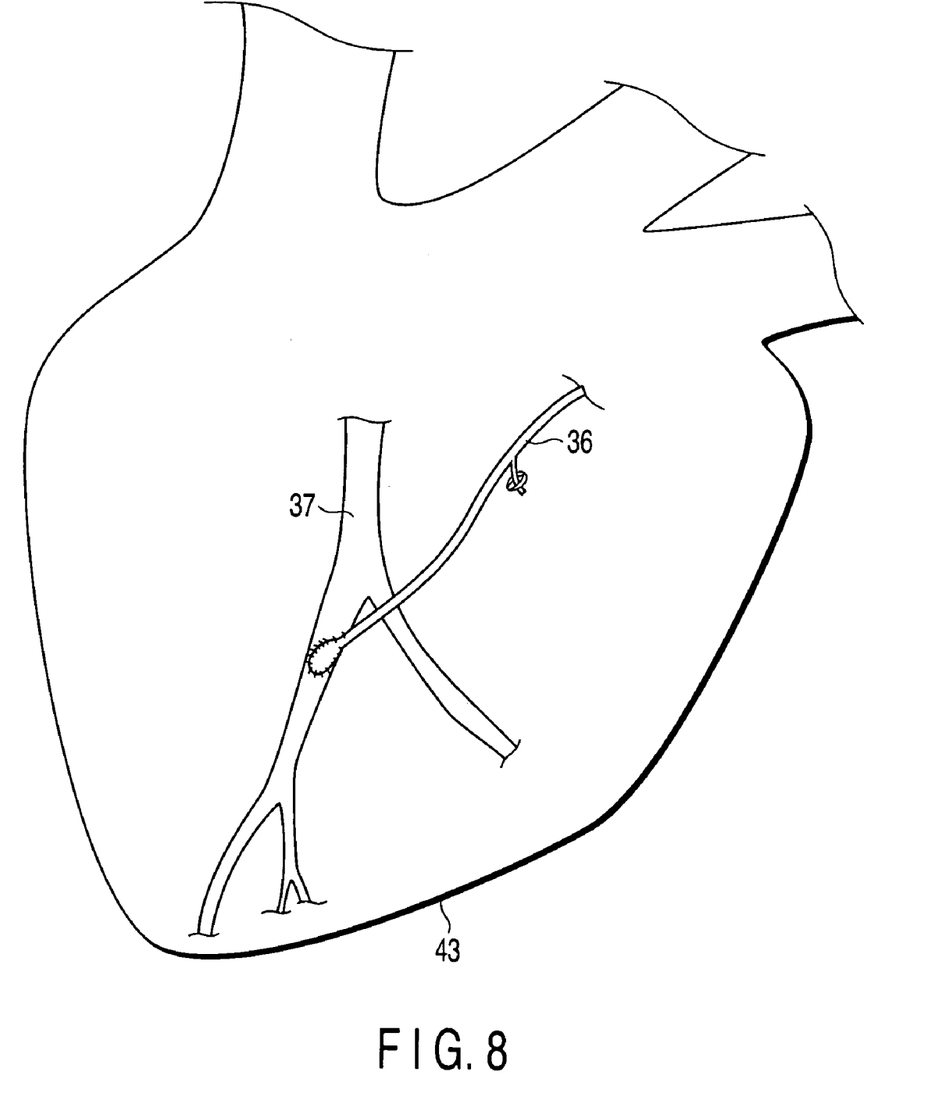
FIG. 8 is a diagram illustrating the heart after treatment by the blood vessel treatment method according to the embodiment of the present invention.

FIG. 8 illustrates a heart 43 after treatment by the above heart coronary artery bypass operation.

The multi-degree-of-freedom forceps 12 used in the embodiment enables deliberate and delicate treatment since the tip working portion 20 has a high degree of freedom. Therefore, a blood vessel can be deliberately and delicately treated in the blood vessel treatment method of the embodiment. This prevents injury to the blood vessel, and prevents a serious situation caused by hemorrhage and the like. Further, the multi-degree-of-freedom forceps 12 used in the embodiment can be held and manipulated by one hand, and can be easily removed from the body cavity from the state of being inserted into the body cavity. Therefore, according to the blood vessel treatment method in the embodiment, even if a contingency such as hemorrhage occurs, it is possible to smoothly proceed to thoracotomy or laparotomy, by promptly removing the multi-degree-of-freedom forceps 12 from the body cavity.

Further, according to the blood vessel treatment method of the embodiment, the tip working portion 20 is temporarily positioned by holding and manipulating the handle 22, and the tip working portion 20 is driven in the vertical and horizontal directions to perform treatment, by rotating the track ball 24 in the vertical and horizontal directions. This allows intuitive operation of the tip working portion 20 and reduces unnecessary displacement of the tip working portion 20, and thereby deliberate and delicate treatment is enabled. Therefore, it is possible to treat blood vessels safely and securely.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A blood vessel treatment method using multi-degree-of-freedom forceps, the method comprising:
providing a multi-degree-of-freedom forceps comprising a forceps main body and a controller, the forceps main body including an elongated inserting portion, a joint portion provided on a distal end portion of the inserting portion, a tip working portion which is connected to the joint portion and driven with at least 2 degrees of freedom including a vertical direction which is normal to a central axis of the elongated inserting portion, by activation of the joint portion, a handle provided on a proximal end portion of the inserting portion, which includes an actuator activating the joint portion and the tip working portion and which is held and manipulated using the fingers of one hand, and an input portion provided on the handle, the controller transmitting an electric signal to the actuator and driving the joint portion and the tip working portion in response to an input to the input portion;
incising a membranous tissue covering a blood vessel by an input to the input portion, using the fingers of one hand so that the joint portion causes a blade of an electric cautery used as the tip working portion to move in the horizontal direction and so that the tip working portion is supplied with electricity, in a state where a distal side of the forceps main body is inserted into a body cavity; and
detaching the blood vessel from a tissue by an input to the input portion, using the fingers of one hand so that the joint portion causes the blade to move in the vertical direction, in a state where the distal side of the forceps main body is inserted into the body cavity through an incised portion of the membranous tissue.

2. A blood vessel treatment method according to claim 1, further comprising:
anastomosing a stump portion of the blood vessel to another blood vessel by an input to the input portion, in a state where the distal side of the forceps main body is inserted into the body cavity.

3. A blood vessel treatment method according to claim 1, further comprising:
cutting off a branch from the blood vessel by an input to the input portion, using the fingers of one hand so that the tip working portion is rotated about the central axis of the tip working portion to be substantially perpendicular to a running direction of the branch, in a state where the distal side of the forceps main body is inserted into the body cavity.

4. A blood vessel treatment method according to claim 3, wherein
the cutting off the branch includes cutting off by using scissors as the tip working portion.

5. A blood vessel treatment method according to claim 3, wherein
the cutting off the branch includes providing hemostasis of the branch on both sides of a region to be cut, before cutting off the branch.

6. A blood vessel treatment method according to claim 5, wherein
the providing hemostasis includes providing hemostasis by using clips.

7. A blood vessel treatment method according to claim 3, further comprising:
cutting off a peripheral side of the blood vessel by an input to the input portion, using the fingers of one hand so that the joint portion causes the tip working portion to move in the horizontal and vertical directions, thereby positioning the tip working portion to be substantially perpendicular to a running direction of the blood vessel, in a state where the distal side of the forceps main body is inserted into the body cavity.

8. A blood vessel treatment method according to claim 1, further comprising:
cutting off a peripheral side of the blood vessel by an input to the input portion, using the fingers of one hand so that the joint portion causes the tip working portion to move in the horizontal and vertical directions, thereby positioning the tip working portion to be substantially perpendicular to a running direction of the blood vessel, in a state where the distal side of the forceps main body is inserted into the body cavity.

9. A blood vessel treatment method according to claim 8, wherein
the cutting off the peripheral side of the blood vessel includes cutting off by using scissors as the tip working portion.

10. A blood vessel treatment method according to claim 8, wherein
the cutting off the peripheral side of the blood vessel includes providing hemostasis of the blood vessel on both sides of a region to be cut, before cutting off the peripheral side.

11. A blood vessel treatment method according to claim 10, wherein
the providing hemostasis includes providing hemostasis by using clips.

12. A blood vessel treatment method according to claim 1, wherein
the degree of freedom of the tip working portion includes 2 degrees of freedom perpendicular to a longitudinal direction of the inserting portion.

13. A blood vessel treatment method according to claim 12, wherein
the input portion includes a track ball which drives the tip working portion with 2 degrees of freedom perpendicular to the longitudinal direction.

14. A blood vessel treatment method according to claim 12, wherein
the input portion includes a pressure sensor which drives the tip working portion with a magnitude corresponding to a pressure applied to the input portion.

15. A blood vessel treatment method using multi-degree-of-freedom forceps,
the method comprising:
providing a multi-degree-of-freedom forceps comprising a forceps main body and a controller, the forceps main body including an elongated inserting portion, a joint portion provided on a distal end portion of the inserting portion, a tip working portion which is connected to the joint portion and driven with at least 2 degrees of freedom including a horizontal direction and a vertical direction which are normal to a central axis of the elongated inserting portion, by activation of the joint portion, a handle provided on a proximal end portion of the inserting portion, which includes an actuator activating the joint portion and the tip working portion and which is held and manipulated using the fingers of one hand, and an input portion provided on the handle, the controller transmitting an electric signal to the actuator and driving the joint portion and the tip working portion in response to an input to the input portion;
cutting off a branch from a blood vessel by an input to the input portion using the fingers of one hand so that the joint portion causes the tip working portion to move in the horizontal direction and so that the elongated inserting portion is rotated, thereby rotating the tip working portion about the central axis of the tip working portion and thereby positioning the elongated inserting portion to be substantially perpendicular to a running direction of the branch, in the state where a distal side of the forceps main body is inserted into a body cavity; and cutting off a peripheral side of the blood vessel by an input to the input portion using the fingers of one hand so that the joint portion causes the tip working portion to move in the horizontal and vertical directions, thereby positioning the tip working portion to be substantially perpendicular to a running direction of the blood vessel, in a state where the distal side of the forceps main body is inserted into the body cavity, wherein the cutting off the branch includes cutting off by using scissors as the tip working portion; and the cutting off the peripheral side of the blood vessel includes cutting off by using scissors as the tip working portion.

* * * * *